US00PP08490P

United States Patent [19]

Meier et al.

[11] Patent Number: Plant 8,490

[45] Date of Patent: Dec. 7, 1993

[54] BA 73-540 KENTUCKY BLUEGRASS

[75] Inventors: Virgil D. Meier; Eugene W. Mayer, both of Marysville, Ohio

[73] Assignee: The O. M. Scott & Sons Company, Marysville, Ohio

[21] Appl. No.: 821,403

[22] Filed: Jan. 14, 1992

[51] Int. Cl.[5] ..... A01H 5/00

[52] U.S. Cl. ..... Plt./90.2

[58] Field of Search ..... Plt./90.2

*Primary Examiner*—James R. Feyrer

*Attorney, Agent, or Firm*—Jones, Day, Reavis & Pogue

[57] ABSTRACT

A variety of Kentucky bluegrass having a medium to high level of disease resistance strong sod forming ability, high quality dense persistent turf formation properties under a wide variety of environmental conditions and a medium level of seed yield potential.

4 Drawing Sheets

BACKGROUND

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; U.S. Plant Pat. No. 6,280 which issued on Sep. 6, 1988; U.S. Plant Pat. No. 6,537 which issued on Jan. 17, 1989; U.S. Plant Pat. No. 6,538 which issued on Jan. 17, 1989; 6,585 which issued on Feb. 7, 1989; U.S. Plant Pat. No. 7,831 which issued on Mar. 17, 1992 and U.S. Plant patent application Ser. No. 792,173, which was filed on Nov. 14, 1991, now abandoned.

SUMMARY OF THE VARIETY

The present invention relates to a new and improved variety of Kentucky bluegrass, *Poa pratensis*, that has been designated Ba 73-540.

Ba 73-540 plant material originated by crossing two Kentucky bluegrass plants maintained in the O. M. Scott & Sons Company plant nursery. The female parent plant for the present variety was a Kentucky bluegrass locally identified under the designation Bd 68-486 and the male parent plant was a Kentucky bluegrass locally identified under the designation Bd 64-36-1 in the plant nursery. Neither the Bd 68-486 plant nore the Bd 64-36-1 plant has been released as a commercial variety to date. As a result of this breeding, a distinct variety was produced and asexually propagated by rhizomes, tillers and disseminules. Seed of Ba 73-540 was produced first at Marysville, Ohio and later at Gervais, Oreg. This seed was used to plant turf performance evaluation trails and later seed production fields.

Asexual production of Ba 73-540 by propagules (tillers and rhizomes) and by disseminules (modified caryopses produced by apomixis) has consistently produced progeny plants indistinguishable from the mother plant. The apomixis level of Ba 73-540 is 100% based upon examining seedling characteristics of approximately 130 to 140 seedlings from four different crop years in a growth chamber.

Ba 73-540 has a number of highly desirable characteristics including a good level of resistance to Drechslera spp. (formerly called Helminthosporium spp.) that causes leaf spot, melting out and crown rot; *Sclerotinia homoeocarpa* that causes dollar spot; Puccinia spp. that causes several types of rust infections and *Erysiphe graminis* that causes powdery mildew. Ba 73-540 has an attractive leafy turf type growth habit; moderately wide leaf blades; an attractive green color which can be maintained throughout the entire growing season; good drought and heat tolerance and good turf performance as evidenced by consistently high scores for quality, color and density in National Turfgrass Evaluation Tests sponsored by the U.S. Department of Agriculture and conducted throughout the U.S.A. and Canada. Ba 73-540 has a medium seed yield potential in the bluegrass seed production region of the U.S.A.

In comparison with a number of other Kentucky bluegrasses, Ba 73-540 has a small seed, high seed count, the shortest and narrowest panicle, a short, narrow and thin flag leaf, a short and narrow peduncle, the shortest culm and the shortest and narrowest leaf blade when Ba 73-540 and the other Kentucky bluegrasses are grown as single, spaced plants without competition to the flowering stage. Under close mowing as practiced under lawn maintenance conditions, Ba 73-540 has a leaf blade coarser than a number of other Kentucky bluegrasses which all were treated as uniformly as possible before and during data collection. Thus, in relation to other Kentucky bluegrasses, Ba 73-540 has narrower leaf blades as a mature plant under non-mowed and non-competitive conditions and has coarser leaf blades under mowed and highly competitive conditions. In addition, Ba 73-45 exhibits a high degree of resistance to powdery mildew and various rust diseases. Ba 73-540 is a medium seed yielder.

DETAILED DESCRIPTION OF THE VARIETY

Figure 1:
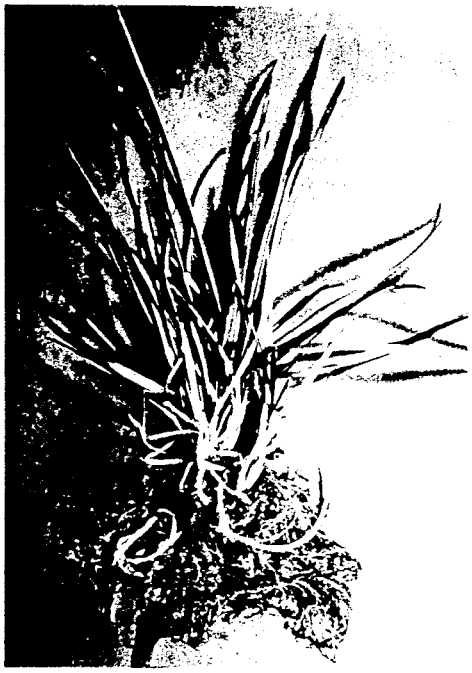
FIG. 1 hows a Ba 73-540 Kentucky bluegrass plant in the vegetative stage including the extensive root and rhizome system.
Figure 2:
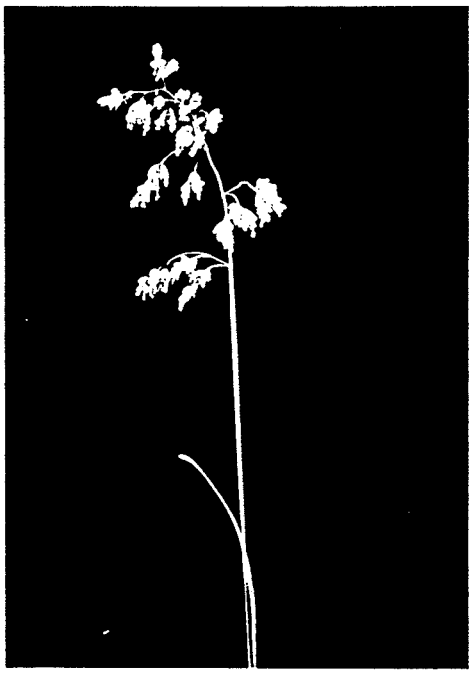
FIG. 2 shows a Ba 73-540 Kentucky bluegrass panicle.
Figure 3:
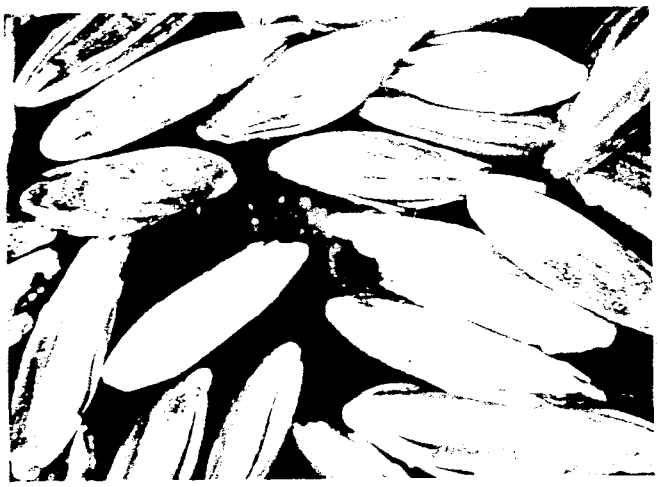
FIG. 3 shows Ba 73-540 Kentucky bluegrass seed.
Figure 4:
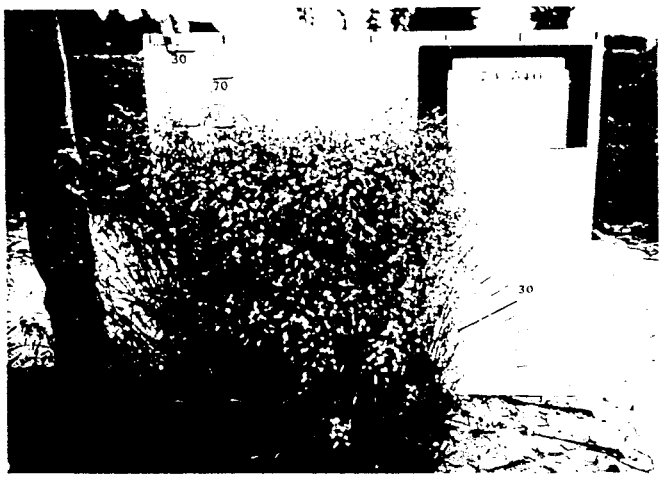
FIG. 4 shows a Ba 73-540 Kentucky bluegrass plant shortly after completing anthesis.

Ba 73-540 Kentucky bluegrass (*Poa pratensis* L.) is perennial with creeping rhizomes forming a dense turf. When plants overwinter in the field with freezing temperatures and are then brought into the greenhouse during late winter to continue growth undisturbed by clipping under moderate temperatures (60°-80° F.), culms are erect averaging 416 mm in length with an average of 2.3 nodes per culm. The uppermost internode averages 10.1 cm, and the peduncle averages 11.4 cm in length, and 0.565 mm in width. The flag leaf averages 4.1 cm in length, 2.8 mm in width and 0.012 mm in thickness. The panicle has an average length of 6.3 cm, width of 3.6 cm, and 4.6 whorls. The lowest whorl has an average of 3.5 branches and the third whorl from the bottom of the panicle has an average of 2.2 branches. The average spikelet at the tip of a branch in the lowest whorl is 5.3 mm in length and has 4.4 florets with an outer glume of 3.0 mm and an inner glume of 3.4 mm in length. A similar spikelet from the third whorl from the bottom of the panicle is 5.2 mm in length and has 4.4 florets with an outer glume of 3.1 mm and an inner glume of 3.4 mm in length. After the seed has been conditioned, the lemma has a generally smooth keel with occasional short hairs and a few long fine hairs at the base. The seed of Ba 73-540 is 2.80 mm in length and 0.78 mm in width with approximately 1,357,914 seeds per pound. Comparisons of Ba 73-540 with other varieties in terms of seed dimensions and on seed numbers per pound are shown in Tables 1 and 2 as follows:

TABLE 1

Seed Measurements of Ba 73-540 and Other Bluegrass Varieties After Conditioning.

| Variety | Length (mm) | Width (mm) |
|---|---|---|
| Ba 73-540 | 2.80 | 0.78 |
| Kelly | 2.98 | 0.80 |
| Abbey | 3.18 | 0.88 |
| Coventry | 2.86 | 0.78 |
| Estate | 2.53 | 0.76 |
| Chateau | 2.77 | 0.80 |
| Baron | 3.07 | 0.86 |
| Bristol | 2.73 | 0.80 |
| Marquis | 2.84 | 0.78 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD (.05) | 0.19 | 0.06 |

t,70

Since environmental conditions such as soil and climate may influence morphological characteristics to some extent, comparisons of morphological characteristics of Ba 73-450 are made with other Kentucky bluegrass varieties in Tables 3–10.

TABLE 3

Morphological Comparison of Panicles of Ba 73-540 and Other Bluegrass Varieties in the Greenhouse at Marysville, Ohio

| Variety | Panicle Nodding* | Panicle Length (cm) | Panicle Width (cm) | Number of Whorls Per Panicle | Number of Branches: Lower Whorl | Number of Branches: Third Whorl |
|---|---|---|---|---|---|---|
| Ba 73-540 | 2.0 | 6.3 | 3.6 | 4.6 | 3.5 | 2.2 |
| Kelly | 1.3 | 9.7 | 6.0 | 5.5 | 4.5 | 3.4 |
| Abbey | 1.4 | 7.6 | 4.2 | 5.2 | 4.0 | 2.7 |
| Baron | 1.0 | 7.8 | 4.1 | 5.2 | 3.8 | 2.5 |
| Bristol | 2.0 | 9.7 | 5.0 | 5.0 | 3.3 | 2.7 |
| Chateau | 2.0 | 6.8 | 3.8 | 5.0 | 4.0 | 2.4 |
| Coventry | 2.0 | 6.7 | 3.7 | 4.8 | 3.8 | 2.7 |
| Estate | 1.2 | 7.5 | 4.2 | 5.5 | 4.0 | 3.0 |
| Marquis | 1.7 | 7.8 | 4.5 | 5.2 | 4.1 | 3.1 |
| Nassau | 2.0 | 10.0 | 6.0 | 5.0 | 3.0 | 2.0 |
| Newport | 2.0 | 10.3 | 4.4 | 4.5 | 2.3 | 2.3 |
| Park | 1.6 | 9.0 | 3.7 | 4.0 | 4.3 | 3.7 |
| Ram I | 2.0 | 9.0 | 4.7 | 4.0 | 2.5 | 2.0 |
| Victa | 1.2 | 7.5 | 4.1 | 5.4 | 4.4 | 3.4 |

TABLE 3-continued

Morphological Comparison of Panicles of Ba 73-540 and Other Bluegrass Varieties in the Greenhouse at Marysville, Ohio

| Variety | Panicle Nodding* | Panicle Length (cm) | Panicle Width (cm) | Number of Whorls Per Panicle | Number of Branches: Lower Whorl | Number of Branches: Third Whorl |
|---|---|---|---|---|---|---|
| LSD (.05) | 0.5 | 1.6 | 1.0 | 0.8 | 0.7 | 0.8 |

*Panicle nodding rated: 1 = erect, 2 = nodding

TABLE 4

Morphological Comparison of Spikelets of Ba 73-540 and Other Bluegrass Varieties in the Greenhouse at Marysville, Ohio.

| Variety | Spikelet Length (mm): Lowest Whorl | Spikelet Length (mm): Third Whorl | Number of Florets per Spikelet: Lowest Whorl | Number of Florets per Spikelet: Third Whorl |
|---|---|---|---|---|
| Ba 73-540 | 5.3 | 5.2 | 4.4 | 4.4 |
| Kelly | 5.8 | 5.6 | 4.4 | 4.1 |
| Abbey | 5.1 | 5.0 | 3.9 | 3.8 |
| Baron | 5.0 | 5.0 | 3.7 | 3.8 |
| Bristol | 6.2 | 6.0 | 5.7 | 5.3 |
| Chateau | 5.1 | 5.0 | 4.2 | 3.9 |
| Coventry | 5.2 | 5.2 | 4.2 | 4.0 |
| Estate | 5.2 | 5.0 | 4.2 | 4.2 |
| Marquis | 5.4 | 5.2 | 4.1 | 3.9 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD (.05) | 0.9 | 0.8 | 1.1 | 1.0 |

TABLE 5

Morphological Comparison of Glumes of Ba 73-540 and Other Bluegrass Varieties in the Greenhouse at Marysville, Ohio.

| Variety | Glume Length (mm): Outer: Lowest Whorl | Glume Length (mm): Outer: Third Whorl | Glume Length (mm): Inner: Lowest Whorl | Glume Length (mm): Inner: Third Whorl |
|---|---|---|---|---|
| Ba 73-540 | 3.0 | 3.1 | 3.4 | 3.4 |
| Kelly | 3.2 | 3.3 | 3.7 | 3.6 |
| Abbey | 2.9 | 2.9 | 3.3 | 3.3 |
| Baron | 2.9 | 2.8 | 3.4 | 3.3 |
| Bristol | 3.4 | 3.3 | 3.7 | 3.9 |
| Chateau | 3.1 | 3.1 | 3.4 | 3.4 |
| Coventry | 3.2 | 3.1 | 3.5 | 3.5 |
| Estate | 2.9 | 3.0 | 3.3 | 3.3 |
| Marquis | 2.9 | 2.8 | 3.3 | 3.2 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |
| LSD (.05) | 0.5 | 0.4 | 0.4 | 0.4 |

TABLE 6

Morphological Comparison of Flag Leaves of Ba 73-540 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 73-540 | 4.1 | 2.8 | 0.102 |
| Kelly | 5.8 | 4.2 | 0.119 |
| Abbey | 4.3 | 3.3 | 0.107 |
| Baron | 4.5 | 3.2 | 0.119 |
| Bristol | 5.5 | 3.4 | 0.127 |
| Chateau | 4.1 | 3.2 | 0.111 |

TABLE 6-continued

Morphological Comparison of Flag Leaves of Ba 73-540 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Coventry | 4.7 | 3.2 | 0.112 |
| Estate | 5.2 | 3.6 | 0.117 |
| Marquis | 4.7 | 3.6 | 0.112 |
| Nassau | 6.2 | 3.1 | 0.127 |
| Newport | 6.1 | 3.5 | 0.135 |
| Park | 4.2 | 2.6 | 0.110 |
| Ram I | 4.7 | 3.1 | 0.127 |
| Victa | 5.9 | 4.0 | 0.124 |
| LSD (.05) | 1.8 | 0.6 | 0.013 |

TABLE 7

Morphological Comparison of Peduncles, Culms, and Internodes of Ba 73-540 and Other Bluegrass Varieties in the Greenhouse at Marysville, Ohio.

| Variety | Peduncle Length (cm) | Peduncle Width (mm) | Culm Length (mm) | Number of Nodes Per Culm | Top Internode Length (cm) |
|---|---|---|---|---|---|
| Ba 73-540 | 11.4 | 0.565 | 416 | 2.3 | 10.1 |
| Kelly | 12.3 | 0.772 | 514 | 2.3 | 12.4 |
| Abbey | 10.6 | 0.564 | 421 | 2.7 | 9.3 |
| Baron | 12.7 | 0.555 | 482 | 2.5 | 10.1 |
| Bristol | 15.0 | 0.677 | 522 | 2.7 | 11.3 |
| Chateau | 12.9 | 0.654 | 439 | 2.7 | 9.8 |
| Coventry | 13.2 | 0.607 | 435 | 2.7 | 10.2 |
| Estate | 12.6 | 0.552 | 486 | 2.2 | 10.5 |
| Marquis | 11.4 | 0.667 | 434 | 2.6 | 9.5 |
| Nassau | 8.0 | 0.546 | 450 | 2.5 | 11.2 |
| Newport | 18.0 | 0.567 | 547 | 2.3 | 11.2 |
| Park | 14.3 | 0.779 | 578 | 3.0 | 13.0 |
| Ram I | 18.5 | 0.622 | 527 | 3.0 | 10.2 |
| Victa | 12.2 | 0.716 | 474 | 2.4 | 10.6 |
| LSD (.05) | 3.7 | 0.018 | 79 | 0.6 | 2.1 |

TABLE 8

Morphological Comparison of Leaves of Ba 73-540 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 73-540 | 0.22 | 186 | 3.8 | 50 |
| Kelly | 0.29 | 215 | 4.4 | 46 |
| Abbey | 0.23 | 218 | 3.9 | 56 |
| Baron | 0.30 | 313 | 4.4 | 63 |
| Bristol | 0.30 | 253 | 4.3 | 37 |
| Chateau | 0.25 | 204 | 4.1 | 50 |
| Coventry | 0.26 | 218 | 4.1 | 55 |
| Estate | 0.28 | 239 | 4.4 | 52 |
| Marquis | 0.31 | 215 | 4.2 | 57 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD (.05) | 0.11 | 49 | 0.6 | 10 |

TABLE 9

Morphological Comparision of Leaf Hairs of Ba 73-540 and Other Bluegrass Varieties in the Greenhouse at Marysville, Ohio.

| Variety | Hairs Around Ligule on Upper Surface of the Leaf (a) | Hairs on Collar (a) | Hairs on Ligule (b) |
|---|---|---|---|
| Ba 73-540 | 1.0 | 3.2 | 2.1 |

TABLE 9-continued

Morphological Comparision of Leaf Hairs of Ba 73-540 and Other Bluegrass Varieties in the Greenhouse at Marysville, Ohio.

| Variety | Hairs Around Ligule on Upper Surface of the Leaf (a) | Hairs on Collar (a) | Hairs on Ligule (b) |
|---|---|---|---|
| Kelly | 1.2 | 4.2 | 3.6 |
| Abbey | 1.0 | 3.4 | 2.2 |
| Baron | 1.0 | 5.0 | 4.0 |
| Bristol | 1.3 | 4.7 | 4.3 |
| Chateau | 1.0 | 3.5 | 2.7 |
| Coventry | 1.0 | 3.5 | 1.5 |
| Estate | 1.0 | 3.2 | 1.3 |
| Marquis | 1.2 | 4.4 | 2.6 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD (.05) | 0.3 | 1.4 | 1.8 |

(a) Hairs around ligule and on collar rated 1–4: 1 = none, 5 = many
(b) Hairs on ligule rated 0–5: 0 = none, 5 = many

TABLE 10

Morphological Comparisons of Ba 73-540 and Other Bluegrass Varieties Grown as Unmowed Spaced Plants in the Field at Marysville, Ohio.

| | Mature Plant Height (a) | Panicle Density (b) | Maturity (c) |
|---|---|---|---|
| Ba 73-540 | 54 | 7 | 8 |
| Kelly | 50 | 5 | 8 |
| Abbey | 49 | 5 | 7 |
| Baron | 44 | 5 | 9 |
| Chateau | 49 | 5 | 7 |
| Coventry | 48 | 5 | 7 |
| Marquis | 47 | 5 | 9 |
| Estate | 49 | 5 | 7 |
| Nassau | 46 | 6 | 9 |
| Bristol | 54 | 3 | 8 |
| Merit | 61 | 5 | 9 |
| Glade | 49 | 2 | 9 |
| Ram I | 49 | 3 | 7 |
| Victa | 54 | 6 | 8 |

Ratings:
(a) Mature Plant Height (cm) includes panicle
(b) Panicle Density - 1–10, 10 = high panicle density
(c) Maturity - 1–9, 9 = most mature No discernible differences were noted in flower parts and seed coloration other than those characteristics listed in the above tables.

Ba 73-540 has performed well in regions throughout the U.S.A. and Canada, as exhibited by high turf quality ratings in many different locations in comparison to other varieties. In addition, Ba 73-450 has a pleasant medium green color which can be maintained throughout the growing season and good winter color. Comparisons of Ba 73-540 with other varieties for quality, genetic color and winter color are set forth in Tables 11–13 hereinafter. According to comparisons with the Munsell Book of Colors during mid-June, the color of Ba 73450 leaf blades is in the range of 5 GY 4/4 to 5 GY 4/8 to 7/5 GY 4/4. During the same time period the color of similar leaf blades of several other Kentucky bluegrass varieties—Gnome, Midnight, Bristol and Victa—fall in the same range and as a result were indistinguishable based upon use of this color dictionary. Plant age, time of year, management practices of fertilization, irrigation and mowing also influence this color range. Additional comparisons for leaf texture, and spring, summer and fall density, are presented in Tables 14–17.

TABLE 11

Comparison of Turfgrass Quality of Ba 73-540 and Other Kentucky Bluegrass Varieties at various Locations Over a Four Year Period in the U.S.A. and Canada.

| | Turfgrass Quality - Annual Mean Values (a) | | | |
|---|---|---|---|---|
| Variety | Year 1 | Year 2 | Year 3 | Year 4 |
| Ba 73-540 | 5.8 | 5.9 | 6.0 | 5.8 |
| Abbey | 5.6 | 5.7 | 5.9 | 5.7 |
| Able I | 5.7 | 5.7 | 6.0 | 6.1 |
| Amazon | 5.4 | 5.5 | 5.5 | 5.5 |
| America | 5.8 | 5.9 | 6.1 | 6.2 |
| Aquila | 5.4 | 5.6 | 5.9 | 5.7 |
| A-34 | 5.6 | 5.9 | 6.0 | 6.1 |
| Aspen | 5.6 | 5.7 | 6.0 | 6.2 |
| Asset | 6.0 | 5.9 | 6.2 | 6.2 |
| Baron | 5.8 | 5.6 | 5.9 | 5.8 |
| Barzan | 5.0 | 5.2 | 5.4 | 5.4 |
| Bristol | 5.7 | 6.0 | 6.1 | 6.0 |
| Challenger | 5.8 | 5.9 | 6.0 | 5.9 |
| Chateau | 6.0 | 5.8 | 6.0 | 6.0 |
| Cheri | 5.8 | 5.7 | 6.1 | 5.9 |
| Classic | 5.9 | 5.8 | 6.0 | 5.9 |
| Coventry | 5.8 | 5.8 | 5.9 | 5.8 |
| Eclipse | 5.6 | 5.9 | 6.2 | 6.3 |
| Estate | 5.9 | 5.9 | 5.9 | 5.8 |
| Georgetown | 5.8 | 5.6 | 5.8 | 5.8 |
| Glade | 5.7 | 5.8 | 6.1 | 6.1 |
| Gnome | 5.5 | 5.3 | 5.6 | 5.5 |
| Haga | 5.8 | 5.8 | 5.8 | 5.9 |
| Julia | 5.7 | 5.8 | 5.9 | 5.7 |
| Kelly | 5.6 | 5.7 | 5.9 | 5.8 |
| Kenblue | 5.0 | 4.7 | 5.0 | 5.2 |
| Liberty | 5.7 | 5.7 | 5.8 | 5.7 |
| Marquis | 5.3 | 5.6 | 5.7 | 5.7 |
| Merion | 5.4 | 5.4 | 5.7 | 5.6 |
| Merit | 5.6 | 5.6 | 5.9 | 5.8 |
| Midnight | 6.1 | 6.3 | 6.4 | 6.3 |
| Monopoly | 5.5 | 5.5 | 5.9 | 5.9 |
| Mystic | 5.4 | 5.4 | 5.8 | 6.0 |
| Nassau | 5.6 | 5.7 | 5.8 | 5.5 |
| Parade | 5.7 | 5.7 | 5.9 | 5.8 |
| Ram I | 5.7 | 5.6 | 5.9 | 5.8 |
| Rugby | 6.0 | 5.8 | 5.9 | 5.9 |
| Sydsport | 5.8 | 5.8 | 6.0 | 5.9 |
| Victa | 5.8 | 5.7 | 5.8 | 5.8 |
| Wabash | 5.7 | 5.4 | 5.8 | 5.9 |
| Welcome | 5.3 | 5.5 | 5.7 | 5.5 |
| LSD 0.05 | 0.2 | 0.2 | 0.2 | 0.2 |

(a) Rating Scale 1-9: 9 = ideal turf

TABLE 12

Comparison of Genetic Color of Ba 73-540 and Other Kentucky Bluegrass Varieties at Various Locations Over a Four Year Period in the U.S.A. and Canada.

| | Genetic Color - Annual Mean Values (a) | | | |
|---|---|---|---|---|
| Variety | Year 1 | Year 2 | Year 2 | Year 2 |
| Ba 73-540 | 6.5 | 6.2 | 6.3 | 6.5 |
| Abbey | 6.8 | 6.2 | 6.7 | 6.6 |
| Able I | 7.1 | 6.8 | 6.7 | 6.9 |
| Amazon | 6.2 | 6.9 | 7.0 | 6.5 |
| America | 6.8 | 6.6 | 7.0 | 6.6 |
| Aquila | 6.5 | 6.0 | 6.6 | 6.3 |
| A-34 | 5.7 | 5.6 | 5.7 | 5.7 |
| Aspen | 7.1 | 6.4 | 6.7 | 6.5 |
| Asset | 6.7 | 6.3 | 6.3 | 6.4 |
| Baron | 6.8 | 6.5 | 6.9 | 6.8 |
| Barzan | 6.5 | 6.1 | 6.6 | 6.3 |
| Bristol | 7.3 | 7.1 | 6.6 | 6.6 |
| Challenger | 7.2 | 6.9 | 6.8 | 6.7 |
| Chateau | 6.5 | 6.0 | 6.2 | 6.5 |
| Cheri | 6.6 | 5.9 | 6.3 | 6.3 |
| Classic | 5.8 | 5.6 | 6.3 | 5.9 |
| Coventry | 6.5 | 6.0 | 6.5 | 6.6 |
| Eclipse | 7.7 | 6.7 | 6.5 | 6.6 |
| Estate | 6.7 | 5.9 | 6.3 | 6.6 |
| Georgetown | 6.1 | 5.7 | 5.9 | 5.7 |
| Glade | 7.4 | 7.0 | 6.7 | 6.9 |
| Gnome | 6.4 | 6.5 | 6.8 | 6.7 |
| Haga | 5.8 | 5.5 | 6.1 | 5.8 |

TABLE 12-continued

Comparison of Genetic Color of Ba 73-540 and Other Kentucky Bluegrass Varieties at Various Locations Over a Four Year Period in the U.S.A. and Canada.

| | Genetic Color - Annual Mean Values (a) | | | |
|---|---|---|---|---|
| Variety | Year 1 | Year 2 | Year 2 | Year 2 |
| Julia | 6.4 | 6.3 | 6.7 | 6.3 |
| Kelly | 6.7 | 6.5 | 6.9 | 6.5 |
| Kenblue | 5.2 | 5.2 | 5.5 | 6.0 |
| Liberty | 6.5 | 6.5 | 6.4 | 6.0 |
| Marquis | 7.2 | 6.6 | 6.8 | 6.5 |
| Merion | 6.4 | 5.6 | 6.0 | 6.5 |
| Merit | 6.7 | 6.4 | 6.5 | 6.1 |
| Midnight | 8.0 | 7.9 | 7.5 | 7.7 |
| Monopoly | 5.3 | 5.5 | 5 5 | 5.3 |
| Mystic | 5.9 | 5.6 | 6.3 | 6.0 |
| Nassau | 7.1 | 6.7 | 6.9 | 6.8 |
| Parade | 5.9 | 5.5 | 6.0 | 6.1 |
| Ram I | 6.9 | 6.6 | 6.9 | 6.6 |
| Rugby | 6.2 | 5.4 | 6.1 | 5.8 |
| Sydsport | 6.5 | 6.1 | 6.2 | 6.2 |
| Victa | 6.7 | 6.3 | 6.7 | 6.5 |
| Wabash | 6.0 | 5.1 | 5.7 | 5.3 |
| Welcome | 6.1 | 6.0 | 6.1 | 6.4 |
| LSD (.05) | 0.4 | 0.4 | 0.4 | 0.4 |

(a) Rating Scale 1-9: 9 = dark green

TABLE 13

Comparison of Winter Color of Ba 73-540 and Other Kentucky Bluegrass Varieties in the U.S.A. and Canada.

| | Winter Color - Annual Mean Values (a) | |
|---|---|---|
| Variety | Wichita Kansas Test Location | Agassiz British Columbia Test Location |
| Ba 73-540 | 5.0 | 5.0 |
| Abbey | 3.0 | 4.7 |
| Able I | 5.7 | 4.0 |
| Amazon | 4.0 | 8.7 |
| America | 4.7 | 4.0 |
| Aquila | 3.0 | 4.0 |
| A-34 | 4.7 | 4.3 |
| Aspen | 4.7 | 4.0 |
| Asset | 3.7 | 4.3 |
| Baron | 3.3 | 4.7 |
| Barzon | 4.7 | 5.0 |
| Bristol | 5.7 | 5.0 |
| Challenger | 5.0 | 4.0 |
| Chateau | 5.0 | 5.0 |
| Cheri | 4.3 | 5.0 |
| Classic | 5.0 | 4.0 |
| Coventry | 5.0 | 5.0 |
| Eclipse | 4.0 | 4.3 |
| Estate | 4.3 | 5.0 |
| Georgetown | 5.3 | 4.0 |
| Glade | 3.3 | 4.3 |
| Gnome | 2.7 | 4.3 |
| Haga | 5.0 | 4.0 |
| Julia | 5.0 | 5.0 |
| Kenblue | 3.0 | 3.0 |
| Liberty | 5.0 | — |
| Merion | 3.0 | 4.0 |
| Merit | 3.3 | 5.0 |
| Midnight | 4.3 | 4.7 |
| Monopoly | 3.7 | 4.7 |
| Mystic | 4.0 | 2.0 |
| Nassau | 5.7 | 5.0 |
| Parade | 5.3 | 4.0 |
| Ram I | 5.0 | 4.7 |
| Rugby | 4.7 | 4.3 |
| Sydsport | 4.3 | 5.0 |
| Victa | 3.7 | 5.0 |
| Wabash | 4.7 | 3.3 |
| Welcome | 4.3 | 5.0 |
| LSD (.05) | 1.0 | 0.6 |

(a) Rating Scale: 1-9: 9 = complete color retention.

TABLE 14

Comparison of Leaf Texture of Ba 73-540 and Other Kentucky Bluegrass Varieties at Various Locations Over A Four Year Period in the U.S.A. and Canada.

| Variety | Leaf Texture - Annual Mean Values (a) | | | |
|---|---|---|---|---|
| | Year 1 | Year 2 | Year 3 | Year 4 |
| Ba 73-540 | 5.8 | 5.6 | 5.3 | 4.8 |
| A-34 | 6.4 | 6.9 | 5.7 | 5.2 |
| Abbey | 6.3 | 6.3 | 5.7 | 5.2 |
| Able I | 7.1 | 7.3 | 6.0 | 6.0 |
| Amazon | 7.5 | 7.2 | 6.3 | 5.8 |
| America | 7.1 | 7.2 | 6.0 | 6.7 |
| Aquila | 6.9 | 6.9 | 6.0 | 6.3 |
| Aspen | 6.6 | 6.9 | 5.7 | 5.8 |
| Asset | 6.8 | 6.7 | 6.0 | 6.2 |
| Baron | 6.8 | 6.1 | 6.0 | 5.8 |
| Barzan | 6.1 | 6.7 | 6.0 | 5.7 |
| Bristol | 6.7 | 6.3 | 5.0 | 5.5 |
| Challenger | 6.8 | 6.7 | 5.7 | 5.2 |
| Chateau | 6.1 | 6.0 | 5.7 | 4.8 |
| Cheri | 6.2 | 6.1 | 5.7 | 4.7 |
| Classic | 6.6 | 7.0 | 6.0 | 6.0 |
| Coventry | 5.9 | 5.7 | 5.3 | 4.7 |
| Eclipse | 6.4 | 6.5 | 6.0 | 6.3 |
| Estate | 6.3 | 5.9 | 5.7 | 4.8 |
| Georgetown | 6.8 | 6.8 | 5.3 | 6.0 |
| Glade | 6.8 | 6.7 | 6.0 | 5.7 |
| Gnome | 6.1 | 6.2 | 5.3 | 5.2 |
| Haga | 6.7 | 7.1 | 6.0 | 6.2 |
| Julia | 6.7 | 6.3 | 6.0 | 5.8 |
| Kelly | 6.4 | 5.7 | 5.3 | 5.0 |
| Kenblue | 7.8 | 7.3 | 6.7 | 7.7 |
| Liberty | 6.8 | 6.6 | — | 5.2 |
| Marquis | 6.1 | 5.7 | 5.3 | 5.3 |
| Merion | 6.7 | 6.8 | 6.0 | 5.7 |
| Merit | 6.3 | 6.1 | 6.0 | 5.2 |
| Midnight | 7.3 | 6.7 | 6.0 | 4.8 |
| Monopoly | 7.1 | 6.8 | 6.0 | 6.3 |
| Mystic | 7.4 | 7.5 | 7.3 | 7.8 |
| Nassau | 6.6 | 6.5 | 5.0 | 5.3 |
| Parade | 7.1 | 7.0 | 6.0 | 6.3 |
| Ram I | 7.3 | 7.1 | 6.3 | 4.8 |
| Rugby | 6.8 | 6.7 | 6.0 | 6.2 |
| Sydsport | 5.9 | 5.8 | 6.0 | 5.0 |
| Victa | 6.3 | 6.0 | 5.7 | 5.3 |
| Wabash | 7.1 | 7.2 | 6.3 | 7.7 |
| Welcome | 7.5 | 7.1 | 6.0 | 7.2 |
| LSD 0.05 | 0.5 | 0.5 | 0.6 | 0.7 |

(a) Rating Scale 1-9: 9 = very fine

TABLE 15

Comparison of Spring Density of Ba 73-540 and Other Kentucky Bluegras Varieties at Various Locations in the U.S.A. and Canada Over a Three Year Period.

| Variety | Spring Density - Annual Mean Values (a) | | |
|---|---|---|---|
| | Year 1 | Year 2 | Year 3 |
| Ba 73-540 | 6.3 | 6.5 | 7.6 |
| Abbey | 6.3 | 5.8 | 6.8 |
| Able I | 5.4 | 5.8 | 7.4 |
| Amazon | 6.7 | 6.7 | 6.7 |
| America | 7.0 | 6.2 | 7.1 |
| Aquilla | 5.9 | 6.5 | 6.6 |
| A-34 | 6.6 | 5.7 | 7.3 |
| Aspen | 5.7 | 5.5 | 7.4 |
| Asset | 6.0 | 7.5 | 7.7 |
| Baron | 6.1 | 6.3 | 6.8 |
| Barzan | 5.3 | 6.0 | 6.5 |
| Bristol | 5.6 | 5.3 | 6.9 |
| Challenger | 6.4 | 6.0 | 6.9 |
| Chateau | 6.6 | 6.7 | 7.3 |
| Cheri | 6.3 | 7.2 | 7.4 |
| Classic | 6.9 | 5.5 | 7.2 |
| Coventry | 6.7 | 6.5 | 7.1 |
| Eclipse | 6.2 | 5.5 | 7.1 |
| Estate | 6.1 | 6.3 | 7.2 |
| Georgetown | 5.9 | 5.5 | 6.9 |
| Glade | 5.9 | 6.8 | 7.3 |
| Gnome | 5.8 | 6.0 | 6.3 |
| Haga | 6.6 | 5.5 | 7.3 |

TABLE 15-continued

Comparison of Spring Density of Ba 73-540 and Other Kentucky Bluegras Varieties at Various Locations in the U.S.A. and Canada Over a Three Year Period.

| Variety | Spring Density - Annual Mean Values (a) | | |
|---|---|---|---|
| | Year 1 | Year 2 | Year 3 |
| Julia | 6.0 | 6.5 | 7.4 |
| Kelly | 6.1 | 6.3 | 6.7 |
| Kenblue | 5.9 | 6.2 | 6.0 |
| Liberty | 5.9 | 5.5 | 6.8 |
| Marquis | 5.7 | 6.0 | 6.6 |
| Merion | 6.3 | 6.3 | 7.3 |
| Merit | 6.0 | 5.8 | 6.7 |
| Midnight | 6.1 | 6.7 | 7.4 |
| Monopoly | 6.0 | 6.2 | 7.0 |
| Mystic | 6.3 | 6.7 | 6.9 |
| Nassau | 5.7 | 6.2 | 6.6 |
| Parade | 6.2 | 6.0 | 6.9 |
| Ram I | 6.6 | 7.0 | 6.4 |
| Rugby | 5.8 | 5.3 | 7.0 |
| Sydsport | 6.3 | 6.3 | 7.2 |
| Victa | 5.8 | 5.8 | 6.8 |
| Wabash | 6.8 | 6.7 | 7.0 |
| Welcome | 6.2 | 6.0 | 6.6 |
| LSD (.05) | 0.8 | 0.8 | 0.7 |

(a) Rating Scale 1-9: 9 = maximum density

TABLE 16

Comparison of Summer Density of Ba 73-540 and Other Kentucky Bluegrass at Various Locations in Canada and U.S.A. Over a Two Year Period

| Variety | Summer Density - Annual Mean Values (a) | |
|---|---|---|
| | Year 1 | Year 2 |
| Ba 73-540 | 6.7 | 8.2 |
| Abbey | 7.1 | 8.0 |
| Able I | 6.8 | 7.8 |
| Amazon | 6.8 | 8.2 |
| America | 6.8 | 7.7 |
| Aquilla | 6.7 | 8.0 |
| A-34 | 6.8 | 7.8 |
| Aspen | 6.2 | 7.5 |
| Asset | 7.3 | 8.2 |
| Baron | 6.3 | 7.7 |
| Barzan | 5.3 | 7.3 |
| Bristol | 6.4 | 7.8 |
| Challenger | 6.2 | 7.5 |
| Chateau | 7.3 | 8.3 |
| Cheri | 7.0 | 8.0 |
| Classic | 6.3 | 8.0 |
| Coventry | 6.8 | 8.2 |
| Eclipse | 6.3 | 7.7 |
| Estate | 6.6 | 8.2 |
| Georgetown | 5.9 | 7.3 |
| Glade | 6.2 | 8.2 |
| Gnome | 6.3 | 7.3 |
| Haga | 6.3 | 7.7 |
| Julia | 6.1 | 8.3 |
| Kelly | 6.4 | 7.7 |
| Kenblue | 6.1 | 7.2 |
| Liberty | 5.5 | 7.5 |
| Marquis | 6.3 | 7.0 |
| Merion | 6.4 | 7.8 |
| Merit | 6.3 | 7.8 |
| Midnight | 6.5 | 7.8 |
| Monopoly | 5.8 | 7.7 |
| Mystic | 7.3 | 8.0 |
| Nassau | 6.1 | 7.0 |
| Parade | 6.5 | 7.7 |
| Ram I | 6.7 | 7.8 |
| Rugby | 5.6 | 7.5 |
| Sydsport | 6.8 | 8.0 |
| Victa | 6.2 | 8.0 |
| Wabash | 7.1 | 8.7 |
| Welcome | 6.7 | 7.7 |
| LSD (.05) | 0.8 | 0.7 |

(a) Rating Scale 1-9: 9 = maximum density

TABLE 17

Comparison of Fall Density of Ba-540 and Other Kentucky Bluegrass Varieties at Various Locations in the U.S.A. and Canada Over a Three Year Period

| Variety | Fall Density - Annual Mean Values (a) | | |
|---|---|---|---|
| | Year 1 | Year 2 | Year 3 |
| Ba 73-540 | 7.7 | 8.7 | 7.8 |
| Abbey | 7.3 | 7.0 | 7.2 |
| Able I | 6.7 | 8.2 | 7.4 |
| Amazon | 7.0 | 9.0 | 7.8 |
| America | 7.0 | 8.7 | 7.5 |
| Aquilla | 6.7 | 7.5 | 7.8 |
| A-34 | 7.0 | 8.2 | 7.9 |
| Aspen | 6.7 | 7.2 | 7.7 |
| Asset | 6.0 | 8.7 | 7.5 |
| Baron | 7.3 | 8.0 | 7.0 |
| Barzan | 6.0 | 7.8 | 7.3 |
| Bristol | 6.7 | 7.8 | 7.5 |
| Challenger | 6.7 | 8.3 | 7.9 |
| Chateau | 7.7 | 8.2 | 7.5 |
| Cheri | 7.3 | 8.5 | 7.5 |
| Classic | 7.3 | 8.2 | 7.5 |
| Coventry | 7.3 | 9.0 | 7.3 |
| Eclipse | 7.3 | 8.0 | 7.5 |
| Estate | 6.3 | 8.0 | 7.4 |
| Georgetown | 7.3 | 7.3 | 7.1 |
| Glade | 6.0 | 7.8 | 7.6 |
| Gnome | 7.0 | 7.7 | 7.1 |
| Haga | 7.0 | 8.3 | 7.5 |
| Julia | 7.0 | 8.0 | 7.4 |
| Kelly | 7.3 | 7.2 | 7.0 |
| Kenblue | 7.7 | 8.3 | 7.5 |
| Liberty | 6.7 | 8.0 | 7.0 |
| Marquis | 6.0 | 6.2 | 6.8 |
| Merion | 6.3 | 7.3 | 7.3 |
| Merit | 7.0 | 7.2 | 7.0 |
| Midnight | 7.0 | 8.3 | 8.1 |
| Monopoly | 6.7 | 7.5 | 7.1 |
| Mystic | 7.3 | 8.8 | 7.8 |
| Nassau | 6.3 | 6.5 | 7.3 |
| Parade | 7.0 | 8.7 | 7.5 |
| Ram I | 8.0 | 9.0 | 7.6 |
| Rugby | 6.3 | 7.8 | 7.3 |
| Sydsport | 7.0 | 8.7 | 7.5 |
| Victa | 7.3 | 7.8 | 7.1 |
| Wabash | 7.7 | 9.0 | 8.1 |
| Welcome | 7.7 | 9.0 | 7.7 |
| LSD (.05) | 1.4 | 0.5 | 0.6 |

(a) Rating Scale 1-9: 9 = maximum density

Turf diseases are one of the major causes of inconsistent and poor turf performance. Ba 73-540 has been found to have a high level of resistance to a serious bluegrass disease known as leaf spot (also known as melting out) caused by *Drechslera poae* (formerly called *Helminthosporium vagans*); a medium to high level of resistance to several rust diseases caused by Puccinia spp.; and a medium to high level of resistance to dollarspot caused by *Sclerotina homoeocarpa,* to snow mold caused by *Typhula incarnata* and to powdery mildew caused by *Erysiphe graminis.* Comparisons of disease incidence of Ba 73-540 as compared with other varieties in regard to leaf spot, rusts, dollarspot, snow mold and powdery mildew are presented in Tables 18–23. Additional comparisons are presented in Tables 24–27 for browning due to heat and drought stress, sod strength and seed yields.

TABLE 18

Comparison of Leaf Spot Disease Incidence of Ba 73-540 and other Kentucky Bluegrass Varieties at Various Locations in the U.S.A. and Canada Over a Four Year Period

| Variety | Leaf Spot - Annual Mean Values (a) | | | |
|---|---|---|---|---|
| | Year 1 | Year 2 | Year 3 | Year 4 |
| Ba 73-540 | 5.9 | 5.7 | 6.7 | 6.0 |

TABLE 18-continued

Comparison of Leaf Spot Disease Incidence of Ba 73-540 and other Kentucky Bluegrass Varieties at Various Locations in the U.S.A. and Canada Over a Four Year Period

| Variety | Leaf Spot - Annual Mean Values (a) | | | |
|---|---|---|---|---|
| | Year 1 | Year 2 | Year 3 | Year 4 |
| Abbey | 4.6 | 5.8 | 6.0 | 5.3 |
| Able I | 6.8 | 5.7 | 6.0 | 8.0 |
| Amazon | 5.2 | 5.8 | 6.3 | 7.0 |
| America | 5.7 | 6.5 | 6.0 | 6.3 |
| Aquilla | 6.3 | 4.3 | 6.0 | 3.7 |
| A-34 | 6.3 | 5.7 | 5.8 | 6.3 |
| Aspen | 6.6 | 6.3 | 6.0 | 6.3 |
| Asset | 6.7 | 5.7 | 6.3 | 6.0 |
| Baron | 6.0 | 6.5 | 6.0 | 5.3 |
| Barzan | 6.4 | 5.3 | 6.3 | 1.3 |
| Bristol | 7.9 | 6.5 | 5.7 | 5.3 |
| Challenger | 7.2 | 6.7 | 6.3 | 5.0 |
| Chateau | 6.4 | 6.2 | 6.3 | 6.3 |
| Cheri | 5.7 | 5.7 | 6.7 | 4.7 |
| Classic | 6.2 | 6.0 | 6.3 | 4.3 |
| Coventry | 5.0 | 6.2 | 5.7 | 6.0 |
| Eclipse | 7.4 | 7.0 | 6.7 | 7.7 |
| Estate | 6.8 | 5.8 | 6.3 | 6.7 |
| Georgetown | 6.7 | 6.5 | 5.7 | 4.3 |
| Glade | 7.4 | 5.8 | 6.3 | 7.0 |
| Gnome | 6.0 | 6.3 | 6.0 | 4.3 |
| Haga | 6.7 | 6.0 | 6.0 | 4.7 |
| Julia | 6.0 | 6.0 | 6.7 | 4.7 |
| Kelly | 5.1 | 6.2 | 6.0 | 5.0 |
| Kenblue | 4.8 | 2.0 | 5.3 | 1.0 |
| Liberty | 6.9 | 6.3 | — | 5.3 |
| Marquis | 6.4 | 6.2 | 6.3 | 4.7 |
| Merion | 6.2 | 6.3 | 6.7 | 3.7 |
| Merit | 5.6 | 6.5 | 5.7 | 5.0 |
| Midnight | 7.2 | 6.2 | 6.3 | 6.3 |
| Monopoly | 5.6 | 5.7 | 6.7 | 3.3 |
| Mystic | 5.6 | 5.0 | 5.7 | 5.7 |
| Nassau | 6.6 | 6.2 | 6.3 | 5.3 |
| Parade | 5.3 | 5.3 | 6.0 | 5.0 |
| Ram I | 4.9 | 5.0 | 6.3 | 2.3 |
| Rugby | 6.4 | 5.8 | 6.3 | 4.3 |
| Sydsport | 6.7 | 6.5 | 6.3 | 6.3 |
| Victa | 6.0 | 6.2 | 6.7 | 4.7 |
| Wabash | 4.2 | 2.3 | 5.3 | 2.0 |
| Welcome | 5.2 | 4.8 | 6.0 | 3.7 |
| LSD (.05) | 1.0 | 0.9 | 0.9 | 1.6 |

(a) Rating Scale 1-9: 9 = maximum density

TABLE 19

Comparison of Melting Out Disease Incidence of Ba 73-540 and Other Kentucky Bluegrass Varieties at Various Locations in the U.S.A. and Canada Over a Two Year Period

| Variety | Melting Out - Mean Values (a) | | | |
|---|---|---|---|---|
| | Year 1 | | Year 2 | |
| | Spring (b) | Fall (c) | Spring (d) | Fall Mean (e) |
| Ba 73-540 | 5.2 | 8.7 | 7.3 | 6.3 |
| Abbey | 3.7 | 8.0 | 6.3 | 6.7 |
| Able I | 4.5 | 9.0 | 6.5 | 6.3 |
| Amazon | 4.2 | 7.0 | 7.2 | 6.3 |
| America | 5.2 | 8.7 | 6.8 | 7.0 |
| Aquila | 3.8 | 7.3 | 6.8 | 5.7 |
| A-34 | 4.8 | 8.7 | 6.5 | 6.3 |
| Aspen | 5.0 | 8.7 | 6.2 | 6.0 |
| Asset | 4.7 | 9.0 | 6.8 | 7.0 |
| Baron | 4.3 | 8.3 | 6.5 | 6.3 |
| Barzan | 4.0 | 3.3 | 6.2 | 6.7 |
| Bristol | 5.7 | 9.0 | 6.5 | 6.3 |
| Challenger | 4.8 | 9.0 | 6.5 | 6.0 |
| Chateau | 5.5 | 9.0 | 5.7 | 6.7 |
| Cheri | 4.7 | 8.7 | 6.7 | 6.7 |
| Classic | 6.2 | 8.7 | 6.3 | 6.7 |
| Coventry | 4.3 | 9.0 | 6.2 | 6.7 |
| Eclipse | 5.0 | 7.0 | 7.2 | 7.0 |
| Estate | 5.3 | 9.0 | 6.5 | 6.7 |
| Georgetown | 5.8 | 9.0 | 6.0 | 6.0 |
| Glade | 4.5 | 8.0 | 7.3 | 6.7 |

TABLE 19-continued

Comparison of Melting Out Disease Incidence of Ba 73-540 and Other Kentucky Bluegrass Varieties at Various Locations in the U.S.A. and Canada Over a Two Year Period

| | Melting Out - Mean Values (a) | | | |
|---|---|---|---|---|
| | Year 1 | | Year 2 | |
| Variety | Spring (b) | Fall (c) | Spring (d) | Fall Mean (e) |
| Gnome | 4.5 | 8.7 | 6.7 | 6.3 |
| Haga | 6.2 | 9.0 | 6.0 | 6.3 |
| Julia | 6.0 | 9.0 | 6.8 | 6.3 |
| Kelly | 3.8 | 8.3 | 6.5 | 6.3 |
| Kenblue | 3.7 | 1.0 | 4.3 | 5.3 |
| Liberty | 5.5 | 8.7 | 7.7 | — |
| Marquis | 4.8 | 7.7 | 6.7 | 6.0 |
| Merion | 5.0 | 9.0 | 7.0 | 7.0 |
| Merit | 4.2 | 8.3 | 6.3 | 6.3 |
| Midnight | 4.0 | 9.0 | 7.2 | 6.0 |
| Monopoly | 4.5 | 8.0 | 6.5 | 6.7 |
| Mystic | 5.0 | 1.0 | 6.3 | 4.7 |
| Nassau | 5.0 | 9.0 | 6.5 | 7.0 |
| Parade | 5.7 | 9.0 | 6.2 | 6.0 |
| Ram I | 4.5 | 5.3 | 6.3 | 7.0 |
| Rugby | 5.7 | 9.0 | 6.3 | 6.7 |
| Sydsport | 5.5 | 9.0 | 6.5 | 6.7 |
| Victa | 5.2 | 8.0 | 7.2 | 6.7 |
| Wabash | 4.7 | 6.3 | 4.7 | 4.7 |
| Welcome | 3.8 | 1.3 | 6.5 | 7.0 |
| LSD (.05) | 0.7 | 1.6 | 1.1 | 1.0 |

(a) Rating Scale 1–9: 9 = no disease
(b) Test Locations: Blacksburg and Blackstone, Virginia
(c) Test Location: Puyallup, Washington
(d) Test Locations: Agassiz, British Columbia; Post Falls, Idaho
(e) Test Location: Agassiz, British Columbia

TABLE 19

Comparison of Dollar Spot and Powdery Mildew Disease Incidence of Ba 73-540 and Other Kentucky Bluegrass Varieties in the U.S.A.

| Variety | Columbia Missouri Dollar Spot | Adelphia New Jersey Powdery Mildew |
|---|---|---|
| Ba 73-540 | 8.0 | 5.7 |
| Abbey | 7.3 | 1.0 |
| Able I | 7.7 | 6.7 |
| Amazon | 6.7 | 5.0 |
| America | 7.3 | 7.7 |
| Aquila | 7.3 | 8.3 |
| A-34 | 7.3 | 6.7 |
| Aspen | 6.7 | 4.7 |
| Asset | 7.0 | 2.0 |
| Baron | 7.0 | 1.3 |
| Barzan | 6.3 | 8.3 |
| Bristol | 7.7 | 7.0 |
| Challenger | 7.3 | 3.3 |
| Chateau | 6.7 | 5.3 |
| Cheri | 8.0 | 3.3 |
| Classic | 6.3 | 2.7 |
| Coventry | 7.7 | 6.0 |
| Eclipse | 7.7 | 5.0 |
| Estate | 7.3 | 7.0 |
| Georgetown | 7.3 | 2.7 |
| Glade | 7.3 | 3.3 |
| Gnome | 8.0 | 1.0 |
| Haga | 7.3 | 3.0 |
| Julia | 7.7 | 2.0 |
| Kelly | 7.0 | 1.7 |
| Kenblue | 7.3 | 5.0 |
| Liberty | 7.0 | 4.0 |
| Marquis | 7.7 | 1.0 |
| Merion | 7.3 | 1.0 |
| Merit | 6.7 | 1.7 |
| Midnight | 6.7 | 1.7 |
| Monopoly | 7.0 | 6.7 |
| Mystic | 8.0 | 8.0 |
| Nassau | 6.7 | 2.3 |
| Parade | 7.7 | 2.0 |
| Ram I | 6.0 | 6.7 |
| Rugby | 6.7 | 2.7 |
| Sydsport | 7.3 | 6.7 |

TABLE 19-continued

Comparison of Dollar Spot and Powdery Mildew Disease Incidence of Ba 73-540 and Other Kentucky Bluegrass Varieties in the U.S.A.

| Variety | Columbia Missouri Dollar Spot | Adelphia New Jersey Powdery Mildew |
|---|---|---|
| Victa | 7.7 | 1.7 |
| Wabash | 7.3 | 6.7 |
| Welcome | 7.7 | 6.3 |
| LSD (.05) | 1.4 | 1.4 |

(a) Rating Scale 1–9: 9 = no disease

TABLE 21

Comparison of Powdery Mildew Disease Incidence of Ba 73-540 and Other Kentucky Bluegrass Varieties at Marysville, OH.

| | % Mildew (a) | |
|---|---|---|
| Variety | Test 1 | Test 2 |
| Ba 73-540 | 19.2 | 18.3 |
| Adelphi | 29.2 | 24.2 |
| America | 0.0 | |
| Banff | 5.0 | |
| Bristol | 5.8 | 16.7 |
| Classic | 54.2 | |
| Eclipse | 1.7 | |
| Georgetown | 12.5 | |
| Glade | 40.0 | 27.5 |
| Merion | 37.5 | 48.3 |
| Merit | 66.7 | |
| Monopoly | | 7.5 |
| Nassau | 24.2 | 24.2 |
| Newport | 20.0 | |
| Park | 0.8 | 28.3 |
| Ram I | 12.5 | 30.8 |
| Sydsport | 7.5 | |
| Vantage | 12.5 | 15.8 |
| Victa | 56.7 | 45.8 |
| Wabash | | 10.0 |

(a) Mean for three ratings taken during summer months.

TABLE 22

Comparison of Four Rust Disease Incidence of Ba 73-540 and Other Kentucky Bluegrass Varieties at in the U.S.A. and Canada.

| | Stem Rust[a] | | Stripe Rust[a] |
|---|---|---|---|
| Variety | Adelphia, NJ | Post Falls Idaho | Agassiz, British Columbia |
| Ba 73-540 | 8.0 | 8.0 | 8.0 |
| Abbey | 6.3 | 8.3 | 6.3 |
| Able I | 7.0 | 8.0 | 7.3 |
| Amazon | 6.0 | 7.3 | 7.0 |
| America | 8.3 | 7.7 | 8.0 |
| Aquila | 8.0 | 7.0 | 6.7 |
| Aspen | 8.0 | 7.0 | 6.7 |
| Asset | 8.0 | 8.7 | 7.3 |
| A-34 | 8.0 | 8.0 | 7.0 |
| Baron | 7.3 | 8.0 | 7.0 |
| Barzan | 8.0 | 8.0 | 7.0 |
| Bristol | 8.7 | 8.0 | 8.0 |
| Challenger | 7.7 | 8.0 | 6.7 |
| Chateau | 8.3 | 7.3 | 7.3 |
| Cheri | 7.7 | 8.7 | 6.7 |
| Classic | 8.7 | 8.3 | 8.0 |
| Coventry | 8.3 | 8.0 | 8.0 |
| Eclipse | 7.7 | 8.3 | 6.3 |
| Estate | 7.3 | 7.7 | 8.0 |
| Georgetown | 9.0 | 7.7 | 7.0 |
| Glade | 7.7 | 8.0 | 6.0 |
| Gnome | 7.7 | 8.7 | 7.0 |
| Haga | 9.0 | 7.3 | 7.3 |
| Julia | 8.0 | 7.3 | 7.0 |
| Kelly | 7.3 | 8.7 | 5.7 |
| Kenblue | 8.3 | 7.7 | 7.7 |

TABLE 22-continued

Comparison of Four Rust Disease Incidence of Ba 73-540 and Other Kentucky Bluegrass Varieties at in the U.S.A. and Canada.

| | | | |
|---|---|---|---|
| Liberty | 8.3 | 8.0 | — |
| Marquis | 6.3 | 7.7 | 7.3 |
| Merion | 2.7 | 4.0 | 5.3 |
| Merit | 8.0 | 8.0 | 6.7 |
| Midnight | 8.3 | 7.3 | 5.7 |
| Monopoly | 8.0 | 7.3 | 7.3 |
| Mystic | 5.3 | 6.0 | 5.3 |
| Nassau | 7.7 | 8.0 | 7.3 |
| Parade | 9.0 | 7.0 | 7.7 |
| Ram I | 8.7 | 6.7 | 7.0 |
| Rugby | 8.7 | 7.3 | 7.7 |
| Sydsport | 8.0 | 7.7 | 8.0 |
| Victa | 7.7 | 5.7 | 5.7 |
| Wabash | 8.0 | 8.0 | 6.3 |
| Welcome | 7.3 | 7.7 | 7.3 |
| LSD (.05) | 1.0 | 2.0 | 1.2 |

| | Leaf Rust[a] Santa Ana Cal. | Crown Rust[a] Agassiz BC | Crown Rust[a] Columbia Mo. and Ritzville, Wash. |
|---|---|---|---|
| Ba 73-540 | 5.0 | 9.0 | 8.0 |
| Abbey | 3.0 | 7.0 | 6.8 |
| Able I | 2.0 | 8.3 | 7.5 |
| Amazon | 3.0 | 9.0 | 6.7 |
| America | 5.0 | 8.3 | 9.0 |
| Aquila | 3.0 | 7.0 | 9.0 |
| Aspen | 3.7 | 6.0 | 8.2 |
| Asset | 2.7 | 9.0 | 8.8 |
| A-34 | 3.7 | 8.3 | 7.7 |
| Baron | 3.3 | 8.0 | 7.7 |
| Barzan | 5.0 | 8.3 | 8.7 |
| Bristol | 5.3 | 8.3 | 9.0 |
| Challenger | 4.0 | 6.3 | 8.0 |
| Chateau | 4.0 | 9.0 | 9.0 |
| Cheri | 5.3 | 9.0 | 8.7 |
| Classic | 6.3 | 9.0 | 8.2 |
| Coventry | 4.0 | 8.9 | 9.0 |
| Eclipse | 2.0 | 9.0 | 7.5 |
| Estate | 5.0 | 9.0 | 8.2 |
| Georgetown | 5.3 | 8.7 | 7.2 |
| Glade | 5.0 | 6.7 | 8.0 |
| Gnome | 2.7 | 7.7 | 6.5 |
| Haga | 5.7 | 8.0 | 8.7 |
| Julia | 2.0 | 9.0 | 7.0 |
| Kelly | 5.2 | 6.3 | 6.3 |
| Kenblue | 4.0 | 6.7 | 7.0 |
| Liberty | 5.3 | — | 7.7 |
| Marquis | 5.0 | 6.7 | 8.5 |
| Merion | 2.3 | 5.0 | 6.2 |
| Merit | 2.7 | 7.0 | 8.0 |
| Midnight | 4.0 | 6.3 | 6.7 |
| Monopoly | 3.7 | 9.0 | 8.2 |
| Mystic | 3.0 | 7.0 | 7.0 |
| Nassau | 4.3 | 8.3 | 8.8 |
| Parade | 5.3 | 9.0 | 7.2 |
| Ram I | 5.0 | 8.3 | 7.7 |
| Rugby | 5.0 | 8.7 | 8.5 |
| Sydsport | 4.0 | 8.7 | 7.8 |
| Victa | 3.0 | 7.3 | 7.7 |
| Wabash | 4.3 | 7.3 | 7.7 |
| Welcome | 4.7 | 9.0 | 7.5 |
| LSD (.05) | 1.7 | 1.4 | 1.7 |

[a]Rating Scale: 1–9 9 = no disease

TABLE 23

Comparison of Snow Mold Disease Incidence of Ba 73-540 and Other Kentucky Bluegrass Varieties

| Variety | Snowmold[a] East Lansing Michigan |
|---|---|
| Ba 73-540 | 6.7 |
| Abbey | 7.0 |
| Able I | 4.7 |

TABLE 23-continued

Comparison of Snow Mold Disease Incidence of Ba 73-540 and Other Kentucky Bluegrass Varieties

| Variety | Snowmold[a] East Lansing Michigan |
|---|---|
| Amazon | 1.7 |
| America | 3.7 |
| Aquila | 6.0 |
| Aspen | 6.7 |
| Asset | 4.7 |
| A-34 | 5.3 |
| Baron | 5.0 |
| Barzan | 6.7 |
| Bristol | 7.3 |
| Challenger | 6.3 |
| Chateau | 4.3 |
| Cheri | 4.3 |
| Classic | 5.7 |
| Coventry | 4.7 |
| Eclipse | 4.7 |
| Estate | 5.0 |
| Georgetown | 6.7 |
| Glade | 5.7 |
| Gnome | 4.7 |
| Haga | 6.0 |
| Julia | 6.0 |
| Kelly | 6.0 |
| Kenblue | 5.0 |
| Liberty | 5.7 |
| Marquis | 5.0 |
| Merion | 4.0 |
| Merit | 7.3 |
| Midnight | 3.7 |
| Monopoly | 5.0 |
| Mystic | 5.3 |
| Nassau | 6.7 |
| Parade | 6.3 |
| Ram I | 5.3 |
| Rugby | 6.7 |
| Sydsport | 4.3 |
| Victa | 4.7 |
| Wabash | 3.3 |
| Welcome | 4.0 |
| LSD (.05) | 2.5 |

[a]Rating Scale: 1–9 9 = no disease

TABLE 24

Comparison of % Browning of Ba 73-540 and Other Kentucky Bluegrasses Under Heat and Drought Stress at Prince Frederick, Maryland.

| Variety | % Browning Mean[a] |
|---|---|
| Ba 73-540 | 11.3 |
| Adelphi | 20.0 |
| Bristol | 18.7 |
| Cynthia | 36.3 |
| Glade | 20.0 |
| Merion | 28.0 |
| Merit | 28.5 |
| Nugget | 32.5 |
| Park | 24.5 |
| Pascal | 45.0 |
| Vantage | 19.2 |
| Victa | 18.2 |

[a]Mean for two ratings taken in August

TABLE 25

Comparison of Drought Tolerance Ba 73-540 and Other Kentucky Bluegrass Varieties at Various Locations in the U.S.A. and Canada

| Variety | Drought Tolerance[a] |
|---|---|
| Ba 73-540 | 7.7 |
| Abbey | 7.7 |
| Able I | 7.7 |
| Amazon | 7.0 |
| America | 8.0 |

TABLE 25-continued

Comparison of Drought Tolerance Ba 73-540 and Other Kentucky Bluegrass Varieties at Various Locations in the U.S.A. and Canada

| Variety | Drought Tolerance[a] |
|---|---|
| Aquila | 7.3 |
| A-34 | 6.0 |
| Aspen | 7.3 |
| Asset | 7.0 |
| Baron | 7.0 |
| Barzan | 6.0 |
| Bristol | 6.7 |
| Challenger | 8.3 |
| Chateau | 7.0 |
| Cheri | 7.3 |
| Classic | 7.3 |
| Coventry | 7.3 |
| Eclipse | 7.3 |
| Estate | 7.0 |
| Georgetown | 6.7 |
| Glade | 6.7 |
| Gnome | 8.0 |
| Haga | 6.7 |
| Julia | 7.3 |
| Kelly | 7.7 |
| Kenblue | 6.3 |
| Liberty | 7.7 |
| Marquis | 7.7 |
| Merion | 7.3 |
| Merit | 8.0 |
| Midnight | 6.0 |
| Monopoly | 6.7 |
| Mystic | 7.7 |
| Nassau | 8.0 |
| Parade | 5.7 |
| Ram I | 8.7 |
| Rugby | 7.0 |
| Sydsport | 7.0. |
| Victa | 7.7 |
| Wabash | 6.7 |
| Welcome | 7.3 |
| LSD 0.05 | 1.7 |

[a]Rating Scale 1-9: 9 = no dormacy

TABLE 26

Comparison of Sod Strength Eight Months After Planting of Ba 73-540 and Other Kentucky Bluegrasses at Remington, Va.

| Variety | SOD STRENGTH[a] 8 Months |
|---|---|
| Ba 73-540 | 20.3 |
| Abbey | 17.0 |
| Able I | 16.3 |
| Amazon | 18.0 |
| America | 30.7 |
| Aquila | 19.3 |
| A-34 | 21.7 |
| Aspen | 21.7 |
| Asset | 23.7 |

TABLE 26-continued

Comparison of Sod Strength Eight Months After Planting of Ba 73-540 and Other Kentucky Bluegrasses at Remington, Va.

| Variety | SOD STRENGTH[a] 8 Months |
|---|---|
| Baron | 25.7 |
| Barzan | 13.0 |
| Bristol | 24.7 |
| Challenger | 23.0 |
| Chateau | 23.3 |
| Cheri | 28.3 |
| Classic | 23.0 |
| Coventry | 18.0 |
| Eclipse | 22.0 |
| Estate | 23.3 |
| Georgetown | 30.0 |
| Glade | 26.3 |
| Gnome | 22.0 |
| Haga | 22.3 |
| Julia | 12.3 |
| Kenblue | 22.0 |
| Liberty | 20.3 |
| Marquis | 23.0 |
| Merion | 21.3 |
| Merit | 25.3 |
| Midnight | 22.3 |
| Monopoly | 26.0 |
| Mystic | 21.3 |
| Nassau | 22.3 |
| Parade | 26.0 |
| Ram I | 22.3 |
| Rugby | 20.3 |
| Sydsport | 26.0 |
| Victa | 29.3 |
| Wabash | 16.7 |
| Welcome | 24.7 |
| LSD (.05) | 6.9 |

[a]Rating Scale: Kilograms of tension needed to tear sod.

TABLE 27

Seed yield Comparisons in Pounds Per Acre of Ba 73-540 and Other Kentucky Bluegrass Varieties in Oregon Over a Three Year Period

| | Lbs/Acre | | |
|---|---|---|---|
| | Gervais | LaGrande | |
| Variety | Year 1 | Year 2 | Year 3 |
| Ba 73-540 | 859 | 1224 | 993 |
| Bristol | 862 | 1021 | 690 |
| Victa | 1342 | 1425 | 1224 |
| LSD (.05) | | 220 | 160 |

What is claimed is:

1. A variety of Kentucky bluegrass plant, substantially as shown and described, characterized by a medium to high level of resistance to several serious diseases, including leaf spot disease (also known as melting out disease), various rusts, dollarspot, snowmold and powdery mildew; a desirable green color throughout the growing season; a strong sod forming ability; high quality dense persistent turf formation under a wide variety of environmental conditions; and a medium level of seed yielding capacity.

* * * * *

UNITED STATES PATENT AND TRADEMARK OFFICE

CERTIFICATE OF CORRECTION

PATENT NO. : Plant 8,490

DATED : December 7, 1993

INVENTOR(S) : Virgil D. Meier, Eugene W. Mayer

It is certified that error appears in the above-indentified patent and that said Letters Patent is hereby corrected as shown below:

Column 3, line 4, change "0.012" to --0.102--

Column 3, line 47, change "73-450" to --73-540--

Column 6, line 21, change "1-4" to --1-5--

Column 6, line 51, change "73-450" to --73-540--

Column 6, line 58, change "73450" to --73-540

Column 8, line 14, change "55" to --5.5--

Column 8, line 42, change "Barzon" to --Barzan--

Column 9, line 47, delete underlining of "Kentucky Bluegrass Varieties at Various Locations in"

Column 9, line 54, change "Aquilla" to --Aquila--

Column 10, line 27, delete underlining of "Comparison of Summer Density of BA-73-540 and Other"

UNITED STATES PATENT AND TRADEMARK OFFICE

CERTIFICATE OF CORRECTION

PATENT NO. : Plant 8,490

DATED : December 7, 1993

INVENTOR(S) : Virgil D. Meier, Eugene W. Mayer

It is certified that error appears in the above-indentified patent and that said Letters Patent is hereby corrected as shown below:

Col. 1, line 55; col. 10, line 37; col. 11, line 12; and col. 12, line 12, in Tables 15, 16, 17, 18, change "Aquilla" to --Aquila--.

Column 11, line 1, change "-540" to --73-540--

Column 12, line 42, footnote to Table 18, change "9=maximum density" to --9 = no disease--

Column 13, line 32, change "Table 19" to --Table 20--

Column 14, line 1, change "Table 19" to --Table 20--

UNITED STATES PATENT AND TRADEMARK OFFICE

CERTIFICATE OF CORRECTION

PATENT NO. : Plant 8,490

DATED : December 7, 1993

INVENTOR(S) : Virgil D. Meier, Eugene W. Mayer

It is certified that error appears in the above-indentified patent and that said Letters Patent is hereby corrected as shown below:

Column 3, after all of Table 1 and before "t70" insert all of Table 2 as follows:

Comparison of Seed Numbers Per Pound of Ba 73-540 and Other Bluegrass Varieties After Conditioning.

| | Number of Seeds Per Pound |
|---|---|
| Ba 73-540 | 1,357,914 |
| Kelly | 921,166 |
| Abbey | 1,003,037 |
| Coventry | 1,246,200 |
| Estate | 1,275,740 |
| Chateau | 1,300,105 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Eclipse | 1,335,668 |
| Fylking | 1,130,000 |
| Glade | 1,108,441 |
| Marquis | 1,054,642 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |

UNITED STATES PATENT AND TRADEMARK OFFICE

CERTIFICATE OF CORRECTION

PATENT NO. : Plant 8,490

DATED : December 7, 1993

INVENTOR(S) : Virgil D. Meier, Eugene W. Mayer

It is certified that error appears in the above-indentified patent and that said Letters Patent is hereby corrected as shown below:

| | |
|---|---|
| Vantage | 1,555,303 |
| Victa | 1,038,298 |
| Windsor | 1,520,885 |

Signed and Sealed this

Twenty-eight Day of March, 1995

*Attest:*

Bruce Lehman

BRUCE LEHMAN

*Attesting Officer*

*Commissioner of Patents and Trademarks*